United States Patent [19]

Jolly et al.

[11] 4,328,173
[45] May 4, 1982

[54] RESOLUTION OF D,L-CIS AND D,L-TRANS 2,2-DIMETHYL-3-(2,2-DIHALOVINYL)-CYCLOPROPANE-1-CARBOXYLIC ACIDS AND SALTS THEREOF

[75] Inventors: Jean Jolly, Fontenay-sous-Bois; Giuseppe Gigliotti, Paris; Charles Pavan, Nogent-sur-Marne; Jacques Bulidon, Paris, all of France

[73] Assignee: Roussel Uclaf, Paris, France

[21] Appl. No.: 130,994

[22] Filed: Mar. 17, 1980

[30] Foreign Application Priority Data

Apr. 3, 1979 [FR] France ............................ 79 08338

[51] Int. Cl.³ ...................... C07C 61/16; C07B 19/00
[52] U.S. Cl. ............................... 260/501.16; 562/401
[58] Field of Search ................... 562/401; 260/501.16

[56] References Cited

U.S. PATENT DOCUMENTS

| | | | |
|---|---|---|---|
| 3,590,077 | 6/1971 | Muller et al. | 562/401 |
| 3,739,019 | 12/1973 | Horiuchi et al. | 562/401 |
| 3,842,125 | 6/1973 | Ueda et al. | 562/401 |
| 3,879,451 | 4/1975 | Yoshioka et al. | 562/401 |
| 4,014,918 | 3/1977 | Martel | 562/401 |
| 4,024,163 | 5/1977 | Elliott et al. | 260/347.4 |
| 4,229,593 | 10/1980 | Kondo et al. | 562/401 |

Primary Examiner—Nicky Chan
Assistant Examiner—Vera C. Clarke
Attorney, Agent, or Firm—Hammond & Littell, Weissenberger and Muserlian

[57] ABSTRACT

A novel process for the resolution of D,L-cis and D,L-trans 2,2-dimethyl-3-(2,2-dihalovinyl)-cyclopropane-1-carboxylic acids of the formula

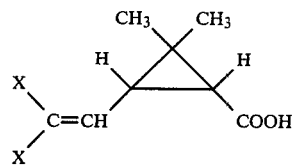

wherein X is selected from the group consisting of fluorine, chlorine and bromine comprising salifying the said acid with an optically active base selected from the group consisting of D-ephedrine, L-ephedrine, D-N-methyl-ephedrine, L-N-methylephedrine, D-pseudo-ephedrine and L-pseudo-ephedrine to form the corresponding salt, recovering the said salt and subjecting the latter to acid hydrolysis to obtain the corresponding resolved acid which are intermediates for the synthesis of esters having a remarkable insecticidal activity.

24 Claims, No Drawings

RESOLUTION OF D,L-CIS AND D,L-TRANS 2,2-DIMETHYL-3-(2,2-DIHALOVINYL)-CYCLOPROPANE-1-CARBOXYLIC ACIDS AND SALTS THEREOF

STATE OF THE ART

Until now, a process for the resolution of D,L-cis 2,2-dimethyl-3-(2,2-dihalovinyl)-cyclopropane-1-carboxylic acids has not been known. Japanese patent applications No. 131,953 (published in 1975) and No. 143,647 and No. 36,441 (both published in 1976) describe processes for the resolution of D,L-trans 2,2-dimethyl-3-(2,2-dichlorovinyl)-cyclopropane-1-carboxylic acid using either D-threo 1-p-nitrophenyl-2-dimethylamino-propane-1,3-diol and other bases not readily available commercially.

OBJECTS OF THE INVENTION

It is an object of the invention to provide a novel process for the resolution of D,L-cis and D,L-trans 2,2-dimethyl-3-(2,2-dihalovinyl)-cyclopropane-1-carboxylic acids in good yields using inexpensive bases.

It is a further object of the invention to provide novel intermediate salts.

These and other objects and advantages of the invention will become obvious from the following detailed description.

THE INVENTION

The novel process of the invention for the resolution of D,L-cis or D,L-trans 2,2-dimethyl-3-(2,2-dihalovinyl)-cyclopropane-1-carboxylic acids of the formula

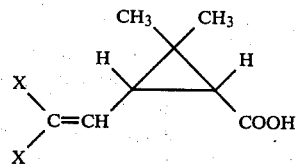

wherein X is selected from the group consisting of fluorine, chlorine and bromine comprises salifying the said acid with an optically active base selected from the group consisting of D-ephedrine, L-ephedrine, D-N-methyl-ephedrine, L-N-methylephedrine, D-pseudo-ephedrine and L-pseudo-ephedrine to form the corresponding salt, recovering the said salt and subjecting the latter to acid hydrolysis to obtain the corresponding resolved acid.

The acid hydrolysis is preferably effected with a strong acid such as hydrochloric acid, hydrobromic acid, sulfuric acid or p-toluene sulfonic acid.

In a preferred mode of the process, D,L-cis 2,2-dimethyl-3-(2,2-dibromovinyl)-cyclopropane-1-carboxylic acid is salified with an optically active base selected from the group consisting of D-ephedrine, L-ephedrine, D-N-methyl-ephedrine and L-N-methyl-ephedrine, recovering the resulting salt and subjecting the latter to acid hydrolysis to obtain D- or L-cis 2,2-dimethyl-3-(2,2-dibromovinyl)-cyclopropane-1-carboxylic acid. Especially preferred are the use of D- or L-ephedrine to form the corresponding L-cis or D-cis acid, respectfully.

The preferred solvent for the said salification reaction is selected from the group consisting of dichloroethane, ethanol, isopropanol and mixtures of isopropyl ether and methanol and especially dichloroethane.

Another preferred process of the invention comprises salifying D,L-cis 2,2-dimethyl-3-(2,2-dibromovinyl)-cyclopropane-1-carboxylic acid with a base selected from the group consisting of D-N-methyl-ephedrine and L-N-methylephedrine, recovering the crystalline salt and subjecting the latter to acid hydrolysis to obtain the D-cis or L-cis 2,2-dimethyl-3-(2,2-dibromovinyl)-cyclopropane-1-carboxylic acid.

The salification is preferably effected in a solvent selected from the group consisting of ethanol, isopropanol, ethyl acetate, dichloroethane, toluene and mixtures of isopropyl ether and methanol. The acid hydrolysis is effected with hydrochloric acid in the presence or absence of an organic solvent, especially isopropyl ether or methyl chloride.

Another preferred process of the invention comprises salifying D,L-cis 2,2-dimethyl-3-(2,2-dichlorovinyl)-cyclopropane-1-carboxylic acid with an optically active base selected from the group consisting of D-ephedrine, L-ephedrine, D-N-methyl-ephedrine, L-N-methylephedrine, D-pseudo-ephedrine and L-pseudo-ephedrine, isolating the crystalline salt and subjecting the latter to acid hydrolysis to obtain the corresponding D-cis or L-cis acid. The preferred base is D-ephedrine or L-ephedrine.

The acid salification is effected with a solvent selected from the group consisting of dichloroethane, ethanol, isopropanol and mixtures of methanol and isopropyl ether.

Another preferred embodiment of the invention comprises salifying D,L-cis 2,2-dimethyl-3-(2,2-dichlorovinyl)-cyclopropane-1-carboxylic acid with an optically active base selected from the group consisting of D-N-methyl-ephedrine and L-N-methyl-ephedrine, recovering the crystalline salt and subjecting the latter to acid hydrolysis to obtain the corresponding D-cis or L-cis acid. The salification is preferably effected in ethyl acetate.

Another preferred embodiment of the invention comprises salifying D,L-cis 2,2-dimethyl-3-(2,2-dichlorovinyl)-cyclopropane-1-carboxylic acid with an optically active base selected from the group consisting of D-pseudoephedrine or L-pseudo-ephedrine, isolating the crystalline salt and subjecting the latter to acid hydrolysis to obtain the corresponding D-cis or L-cis acid. The salification is preferably effected in dichloroethane and the acid hydrolysis of ephedrine, N-methylephedrine or pseudo-ephedrine salt is effected in hydrochloric acid in the optional presence of an organic solvent, especially methylene chloride.

A preferred process of the invention comprises salifying D,L-trans 2,2-dimethyl-3-(2,2-dibromovinyl)-cyclopropane-1-carboxylic acid with an optically active base selected from the group consisting of D-ephedrine and L-ephedrine, recovering the crystalline salt and subjecting the latter to acid hydrolysis to obtain the corresponding D-trans or L-trans acid. The salification is preferably effected in ethanol or dichloroethane.

Another process of the invention comprises salifying D,L-trans 2,2-dimethyl-3-(2,2-dichlorovinyl)-cyclopropane-1-carboxylic acid with an optically active base selected from the group consisting of D-ephedrine and L-ephedrine, recovering the crystalline salt and subjecting the latter to acid hydrolysis to obtain the corresponding D- or L-trans acid. The salification is preferably effected in methyl ethyl ketone.

The acid hydrolysis of ephedrine salts of trans acids is preferably effected with hydrochloric acid in the optional presence of an organic solvent, especially methylene chloride.

In the process, the mother liquors from the crystallization may be evaporated to dryness to recover the salt which did not crystallize and the latter is subjected to acid hydrolysis to obtain the corresponding resolved acid.

The novel intermediates of the invention are the salts of D-cis, L-cis, D-trans and L-trans 2,2-dimethyl-3-(2,2-dihalovinyl)-cyclopropane-1-carboxylic acids of the formula

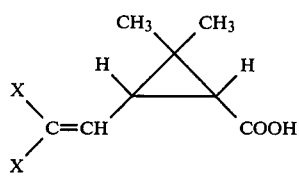

wherein X has the above definition with an optically active base selected from the group consisting of D-ephedrine, L-ephedrine, D-N-methyl-ephedrine, L-N-methyl-ephedrine, D-pseudo-ephedrine and L-pseudo-ephedrine.

In the following examples there are described several preferred embodiments to illustrate the invention. However, it is to be understood that the invention is not intended to be limited to the specific embodiments.

EXAMPLE 1

Resolution of D,L cis 2,2-dimethyl-3-(2,2-dibromovinyl)-cyclopropane-1-carboxylic acid STEP A: L-ephedrine D-cis 2,2-dimethyl-3-(2,2-dibromovinyl)-cyclopropane-1-carboxylate A mixture of 30 g of D,L-cis 2,2-dimethyl-3-(2,2-dibromovinyl)-cyclopropane-1-carboxylic acid, 16.6 g of L-ephedrine and 150 ml of dichloroethane was heated at 70° C. until total dissolution occured and was then cooled over 4 hours to 20° C. The mixture stood at 20° C. for 18 hours and was then vacuum filtered. The recovered precipitate was washed with dichloroethane to obtain 20 g of L-ephedrine D-cis 2,2-dimethyl-3-(2,2-dibromovinyl)-cyclopropane-1-carboxylate.

STEP B: D-cis 2,2-dimethyl-3-(2,2-dibromovinyl)-cyclopropane-1-carboxylic acid 20 g of the salt of Step A were added at about 20° C. to a mixture of 90 ml of isopropyl ether and 60 ml of 2 N hydrochloric acid and the resulting mixture was stirred for 30 minutes while maintaining the pH at 1. The mixture stood for 15 minutes and was decanted. The aqueous phase was extracted with isopropyl ether and the combined organic phases were washed with water and evaporated to dryness to obtain 14 g of product with an acid index of 187 (theory is 188) and a specific rotation of $[\alpha]_D^{20} = +24°$ (c=2% in dimethylformamide). The product was 96.1% of D-cis 2,2-dimethyl-3-(2,2-dibromovinyl)-cyclopropane-1-carboxylic acid and 3.9% of the L-cis acid.

EXAMPLE 2

Using the procedure of Steps A and B of Example 1, 30 g of D,L-cis 2,2-dimethyl-3-(2,2-dibromovinyl)-cyclopropane-1-carboxylic acid, 16.6 g of L-ephedrine and 150 ml of ethanol were reacted to obtain 11.5 g of D-cis 2,2-dimethyl-3-(2,2-dibromovinyl)-cyclopropane-1-carboxylic acid with an acid index of 186 and a specific rotation of $[\alpha]_D^{20} = +25°$ (c=2% in dimethylformamide). The product consisted of 98.1% of the desired D-cis acid and 1.9% of the L-cis acid.

EXAMPLE 3

Using the procedure of Example 1, 30 g of D,L-cis 2,2-dimethyl-3-(2,2-dibromovinyl)-cyclopropane-1-carboxylic acid, 16.6 g of L-ephedrine and 150 ml of isopropanol were reacted to obtain 13.5 g of D-cis 2,2-dimethyl-3-(2,2-dibromovinyl)-cyclopropane-1-carboxylic acid with an acid index of 186 and a specific rotation of $[\alpha]_D^{20} = +24°$ (c=2% in dimethylformamide). The product consisted of 96.1% of the desired D-cis acid and 3.9% of the L-cis acid.

EXAMPLE 4

Using the procedure of Example 1, 30 g of D,L-cis 2,2-dimethyl-3-(2,2-dibromovinyl)-cyclopropane-1-carboxylic acid, 16.6 g of L-ephedrine and 150 ml of a 57-43 isopropyl ether-methanol mixture were reacted to obtain 9 g of D-cis 2,2-dimethyl-3-(2,2-dibromovinyl)-cyclopropane-1-carboxylic acid with an acid index—of 188 and a specific rotation of $[\alpha]_D^{20} = +24.5°$ (c=2% in dimethylformamide). The product consisted of 97.1% of the desired D-cis acid and 2.9% of the L-cis acid.

EXAMPLE 5

Using the procedure of Example 1, 30 g of D,L-cis 2,2-dimethyl-3-(2,2-dibromovinyl)-cyclopropane-1-carboxylic acid, 18 g of L-N-methyl-ephedrine and 150 ml of an 8-2 isopropylether-methanol mixture were reacted to obtain 6 g of D-cis 2,2-dimethyl-3-(2,2-dibromovinyl)-cyclopropane-1-carboxylic acid with an acid index—of 190 and a specific rotation of $[\alpha]_D^{20} = +24°$ (c=2% in dimethylformamide). The product consisted of 96.1% of the desired D-cis acid and 3.9% of the L-cis acid.

EXAMPLE 6

Using the procedure of Example 1, 30 g of D,L-cis 2,2-dimethyl-3-(2,2-dibromovinyl)-cyclopropane-1-carboxylic acid, 18 g of L-N-methyl-ephedrine and 150 ml of ethyl acetate were reacted to obtain 11.4 g of D-cis 2,2-dimethyl-3-(2,2-dibromovinyl)-cyclopropane-1-carboxylic acid with an acid index of 188 and a specific rotation of $[\alpha]_D^{20} = +20.5°$ (c=2% in dimethylformamide). The product consisted of 89.4% of the desired D-cis acid and 10.6% of L-cis acid.

EXAMPLE 7

STEP A: D-ephedrine L-cis 2,2-dimethyl-3-(2,2-dichlorovinyl)-cyclopropane-1-carboxylate 7.9 g of D-ephedrine were added to a mixture of 10 g of D,L-cis 2,2-dimethyl-3-(2,2-dichlorovinyl)-cyclopropane-1-carboxylic acid and 100 ml of dichloroethane and after total dissolution occured, crystallization began. The mixture was stirred at 20° C. for one hour and was vacuum filtered. The recovered product was washed with dichloroethane to obtain 9.9 g of product which was crystallized from dichloroethane to obtain 6.6 g of pure D-ephedrine L-cis 2,2-dimethyl-3-(2,2-dichlorovinyl)-cyclopropane-1-carboxylate with a specific rotation of $[\alpha]_D^{20} = +26° \pm 0.5°$ (c=5% in dimethylformamide).

STEP B: L-cis 2,2-dimethyl-3-(2,2-dichlorovinyl)-cyclopropane-1-carboxylic acid A mixture of 5 g of the salt of Step A, 22.5 ml of methylene chloride and 27 ml of N hydrochloric acid was stirred at 20° C. for 15 minutes and the decanted aqueous phase was extracted with methylene chloride. The combined organic phases were washed with water, dried and evaporated to dryness to obtain 2.7 g of L-cis 2,2-dimethyl-3-(2,2-dichlorovinyl)-cyclopropane-1-carboxylic acid with a specific rotation of $[\alpha]_D^{20} = -39° \pm 0.5°$ (c=5% in dimethylformamide).

EXAMPLE 8

Using the procedure of Example 7, 10 g of D,L-cis 2,2-dimethyl-3-(2,2-dichlorovinyl)-cyclopropane-1-carboxylic acid, 7.9 g of L-ephedrine and 200 ml of dichloroethane were reacted to obtain 7.1 g of L-ephedrine salt which was hydrolyzed to obtain 2.9 g of D-cis 2,2-dimethyl-3-(2,2-dichlorovinyl)-cyclopropane-1-carboxylic acid with a specific rotation of $[\alpha]_D^{20} = +36.5°$ (c=5% in dimethylformamide).

EXAMPLE 9

Using the procedure of Example 7, 10 g of D,L-cis 2,2-dimethyl-3-(2,2-dichlorovinyl)-cyclopropane-1-carboxylic acid, 100 ml of ethanol and 7.9 g of L-ephedrine were reacted to obtain 4.6 g of the L-ephedrine salt which was hydrolyzed to obtain 1.95 g of D-cis-2,2-dimethyl-3-(2,2-dichlorovinyl)-cyclopropane-1-carboxylic acid with a specific rotation of $[\alpha]_D^{20} = +36°$ (c=5% in dimethylformamide).

EXAMPLE 10

Using the procedure of Example 7, 10 g of D,L-cis 2,2-dimethyl-3-(2,2-dichlorovinyl)-cyclopropane-1-carboxylic acid, 150 ml of isopropanol and 7.9 g of L-ephedrine were reacted to obtain 6.4 g of the L-ephedrine salt which was hydrolyzed to obtain 2.7 g of D-cis 2,2-dimethyl-3-(2,2-dichlorovinyl)-cyclopropane-1-carboxylic acid with a specific rotation of $[\alpha]_D^{20} = +36.5°$ (c=5% in dimethylformamide).

EXAMPLE 11

Using the procedure of Example 7, a mixture of 10 g of D,L-cis 2,2-dimethyl-3-(2,2-dichlorovinyl)-cyclopropane-1-carboxylic acid, 70 ml of a 57-43 isopropyl ether-methanol mixture and 7.9 g of L-ephedrine was reacted to obtain 5 g of the L-ephedrine salt which was hydrolyzed to obtain 2.1 g of D-cis 2,2-dimethyl-3-(2,2-dichlorovinyl)-cyclopropane-1-carboxylic acid with a specific rotation of $[\alpha]_D^{20} = +36°$ (c=5% in dimethylformamide).

EXAMPLE 12

Using the procedure of Example 7, 10 g of D,L-cis 2,2-dimethyl-3-(2,2-dichlorovinyl)-cyclopropane-1-carboxylic acid, 100 ml of ethyl acetate and 8.6 g of D-N-methylephedrine were reacted to obtain 4.8 g of the D-N-methylephedrine salt which was hydrolyzed to obtain 2.6 g of L-cis 2,2-dimethyl-3-(2,2-dichlorovinyl)-cyclopropane-1-carboxylic acid with a specific rotation of $[\alpha]_D^{20} = -33°$ (c=5% in dimethylformamide).

EXAMPLE 13

Using the procedure of Example 7, 10 g of D,L-cis 2,2-dimethyl-3-(2,2-dichlorovinyl)-cyclopropane-1-carboxylic acid, 60 ml of dichloroethane and 7.9 g of L-pseudo-ephedrine were reacted to obtain 3.5 g of the corresponding salt which was hydrolyzed to obtain 1.9 g of D-cis 2,2-dimethyl-3-(2,2-dichlorovinyl)-cyclopropane-1-carboxylic acid with a specific rotation of $[\alpha]_D^{20} = +32.5°$ (c=5% in dimethylformamide).

EXAMPLE 14

Resolution of D,L-trans 2,2-dimethyl-3-(2,2-dibromovinyl) cyclopropane-1-carboxylic acid

STEP A: D-ephedrine D-trans 2,2-dimethyl-3-(2,2-dibromovinyl)-cyclopropane-1-carboxylate A mixture of 4 g of D,L-trans 2,2-dimethyl-3-(2,2-dibromovinyl)-cyclopropane-1-carboxylic acid, 2,21 g of D-ephedrine and 40 ml of dichloroethane was stirred until total dissolution occured and then crystallization began. The mixture was stirred at 20° C. for 2 hours and was vacuum filtered. The recovered product was washed with dichloroethane, dried and crystallized from dichloroethane to obtain 2.4 g of D-ephedrine D-trans 2,2-dimethyl-3-(2,2-dibromovinyl)-cyclopropane-1-carboxylate.

STEP B: D-trans 2,2-dimethyl-3-(2,2-dibromovinyl)-cyclopropane-1-carboxylic acid 10 ml of N hydrochloric acid were added with stirring at 20° C. to a mixture of 2.3 g of the salt of Step A and 10 ml of water and the mixture was stirred for 10 minutes. 15 ml of methylene chloride were added to the mixture and the decanted organic phase was washed with water, dried and evaporated to dryness to obtain 1.34 g of D-trans 2,2-dimethyl-3-(2,2-dibromovinyl)-cyclopropane-1-carboxylic acid with a specific rotation of $[\alpha]_D^{20} = +63° \pm 1.5°$ (c=5% in dimethylformamide).

EXAMPLE 15

Using the procedure of Example 14, 4 g of D,L-trans 2,2-dimethyl-3-(2,2-dibromovinyl)-cyclopropane-1-carboxylic acid were reacted with ethanol to obtain after hydrolysis 0.5 g of D-trans 2,2-dimethyl-3-(2,2-dibromovinyl)-cyclopropane-1-carboxylic acid with a specific rotation of $[\alpha]_D^{20} = +63.5° \pm 1.5°$ (c=1% in dimethylformamide).

EXAMPLE 16

STEP A: D-ephedrine L-trans 2,2-dimethyl-3-(2,2-dichlorovinyl)-cyclopropane-1-carboxylate A mixture of 10 g of D,L-trans 2,2-dimethyl-3-(2,2-dichlorovinyl)-cyclopropane-1-carboxylic acid, 7.9 g of D-ephedrine and 60 ml of methyl ethyl ketone was stirred for 2 hours at 20° C. and was vacuum filtered. The recovered product was washed with methyl ethyl ketone, dried and crystallized from methyl ethyl ketone to obtain 1.7 g of D-ephedrine L-trans 2,2-dimethyl-3-(2,2-dichlorovinyl)-cyclopropane-1-carboxylate.

STEP B: L-trans 2,2-dimethyl-3-(2,2-dichlorovinyl)-cyclopropane-1-carboxylic acid A mixture of 1.5 g of the salt of Step A, 10 ml of water and 5 ml of N hydrochloric acid was stirred for 15 minutes and 15 ml of methylene chloride were added thereto. The decanted organic phase was washed with water, dried and evaporated to dryness to obtain 0.7 g of L-trans 2,2-dimethyl-3-(2,2-dichlorovinyl)-cyclopropane-1-carboxylic acid with a specific rotation of $[\alpha]_D^{20} = -64° \pm 1°$ (c=1% in dimethylformamide).

Various modifications of the process of the invention may be made without departing from the spirit or scope thereof and it is to be understood that the invention is intended to be limited only as defined in the appended claims.

We claim:

1. A process for the resolution of D,L-cis and D,L-trans 2,2-dimethyl-3-(2,2-dihalovinyl)-cyclopropane-1-carboxylic acids of the formula

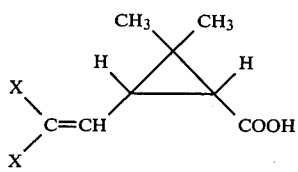

wherein X is selected from the group consisting of fluorine, chlorine and bromine comprising salifying the said acid with an optically active base selected from the group consisting of D-ephedrine, L-ephedrine, D-N-methyl-ephedrine, L-N-methylephedrine, D-pseudo-ephedrine and L-pseudo-ephedrine in a solvent selected from the group consisting of ethanol, isopropanol, toluene, ethyl acetate, dichloroethane, methyl ethyl ketone and mixtures of isopropyl ether and methanol to form the corresponding salt, recovering the said crystallized salt and subjecting the latter to acid hydrolysis to obtain the corresponding resolved acid.

2. A process of claim 1 wherein X is bromine and the base is selected from the group consisting of D-ephedrine, L-ephedrine, D-N-methyl-ephedrine and L-N-methyl-ephedrine and the acid is in the cis form.

3. The process of claim 2 wherein the base is selected from the group consisting of D-ephedrine and L-ephedrine.

4. The process of claim 3 wherein the salification is effected in a solvent selected from the group consisting of dichloroethane, ethanol, isopropanol and mixtures of isopropyl ether and methanol.

5. The process of claim 4 wherein the solvent is dichloroethane.

6. The process of claim 2 wherein the base is selected from the group consisting of D-N-methyl-ephedrine or L-N-methyl ephedrine.

7. The process of claim 6 wherein the salification is effected in a solvent selected from the group consisting of ethanol, isopropanol, toluene, ethyl acetate, dichloroethane and mixtures of isopropyl ether and methanol.

8. The process of claim 2 wherein the acid hydrolysis is effected with hydrochloric acid in the optional presence of an organic solvent.

9. The process of claim 8 wherein the solvent is isopropyl ether or methylene chloride.

10. The process of claim 1 wherein X is chlorine and the optically active base is selected from the group consisting of D-ephedrine, L-ephedrine, D-pseudo-ephedrine, L-pseudo ephedrine, D-N-methyl-ephedrine and L-N-methyl-ephedrine and the acid is in the cis form.

11. The process of claim 10 wherein the base is D-ephedrine or L-ephedrine.

12. The process of claim 11 wherein the salification is effected in a solvent selected from the group consisting of dichloroethane, ethanol, isopropanol and mixtures of isopropyl ether and methanol.

13. The process of claim 10 wherein the base is D-N-methyl-ephedrine or L-N-methyl-ephedrine.

14. The process of claim 13 wherein the salification is effected in ethyl acetate.

15. The process of claim 10 wherein the base is D-pseudo-ephedrine or L-pseudo-ephedrine.

16. The process of claim 15 wherein the salification is effected in dichloroethane.

17. The process of claim 10 wherein the acid hydrolysis is effected with hydrochloric acid.

18. The process of claim 1 wherein X is bromine and the base is selected from the group consisting of D-ephedrine and L-ephedrine and the acid is in the trans form.

19. The process of claim 18 wherein the salification is effected in ethanol or dichloroethane.

20. The process of claim 1 wherein X is chlorine and the base is selected from the group consisting of D-ephedrine and L-ephedrine and the acid is in the trans form.

21. The process of claim 20 wherein the salification is effected in methyl ethyl ketone.

22. The process of claim 18 or 20 wherein the hydrolysis is effected with hydrochloric acid.

23. The process of claim 1 wherein the crystalline mother liquor is evaporated to dryness and the resulting salt which did not crystallize was subjected to acid hydrolysis.

24. A compound selected from the group consisting of the salts of D-cis, L-cis, D-trans and L-trans 2,2-dimethyl-3-(2,2-dihalovinyl)-cyclopropane-1-carboxylic acids of the formula

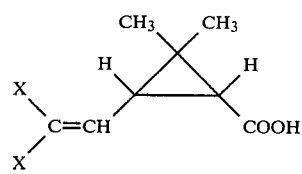

wherein X is selected from the group consisting of fluorine, bromine and chlorine with an optically active base selected from the group consisting of D-ephedrine, L-ephedrine, D-N-methyl-ephedrine, L-N-methylephedrine, D-pseudo-ephedrine and L-pseudo-ephedrine.

* * * * *